(12) United States Patent
Sams et al.

(10) Patent No.: US 10,391,234 B2
(45) Date of Patent: Aug. 27, 2019

(54) TUBING ASSEMBY

(71) Applicant: BAYER HEALTHCARE LLC, Whippany, NJ (US)

(72) Inventors: Stephen Sams, Bassingbourn (GB); Arron Carmo Do Rosario Rodrigues, Cambridge (GB)

(73) Assignee: BAYER HEALTHCARE LLC, Whippany, NJ (US)

( * ) Notice: Subject to any disclaimer, the term of this patent is extended or adjusted under 35 U.S.C. 154(b) by 212 days.

(21) Appl. No.: 15/317,236

(22) PCT Filed: Jun. 8, 2015

(86) PCT No.: PCT/US2015/034656
§ 371 (c)(1),
(2) Date: Dec. 8, 2016

(87) PCT Pub. No.: WO2015/191438
PCT Pub. Date: Dec. 17, 2015

(65) Prior Publication Data
US 2017/0112995 A1    Apr. 27, 2017

Related U.S. Application Data

(60) Provisional application No. 62/009,731, filed on Jun. 9, 2014.

(51) Int. Cl.
*A61M 5/00* (2006.01)
*A61M 5/145* (2006.01)
(Continued)

(52) U.S. Cl.
CPC ........ *A61M 5/007* (2013.01); *A61M 5/14546* (2013.01); *A61M 39/00* (2013.01);
(Continued)

(58) Field of Classification Search
CPC ............ A61M 39/08; A61M 2039/027; A61M 39/284; A61M 39/28; A61M 39/288; A61M 39/00; A61M 2039/244; A61M 2039/0009
See application file for complete search history.

(56) References Cited

U.S. PATENT DOCUMENTS

| | | | |
|---|---|---|---|
| 3,886,937 A | | 6/1975 | Bobo et al. |
| 4,425,113 A | * | 1/1984 | Bilstad .................. A61M 39/28 251/9 |

(Continued)

FOREIGN PATENT DOCUMENTS

| | | | |
|---|---|---|---|
| CA | 2842233 A1 * | 1/2013 | ............ A61M 5/007 |
| EP | 2583716 A1 | 4/2013 | |

(Continued)

OTHER PUBLICATIONS

"International Preliminary Report on Patentability from PCT Application No. PCT/US2015/034656", dated Dec. 22, 2016.
(Continued)

*Primary Examiner* — Bradley J Osinski
*Assistant Examiner* — Nilay J Shah
(74) *Attorney, Agent, or Firm* — David Schramm; Joseph L. Kent; James R. Stevenson

(57) ABSTRACT

A tubing assembly for use with a fluid delivery system has a first fluid line having a distal end and a proximal end for connecting to a first fluid source, and a second fluid line having a distal end and a proximal end for connecting to a second fluid source. The tubing assembly further has a third fluid line having a distal end and a proximal end, and a connector assembly for connecting the distal end of the first fluid line and the distal end of the second fluid line to the proximal end of the third fluid line. A tubing holder receives at least a portion of the third fluid line. The tubing holder has a first portion and a second portion movable relative to the (Continued)

first portion to selectively block fluid flow through the third fluid line.

17 Claims, 6 Drawing Sheets

(51) Int. Cl.
    *A61M 39/00*     (2006.01)
    *A61M 39/08*     (2006.01)
    *A61M 39/10*     (2006.01)
    *A61M 39/24*     (2006.01)
    *A61M 39/28*     (2006.01)
    *A61M 39/22*     (2006.01)

(52) U.S. Cl.
    CPC ........ *A61M 39/08* (2013.01); *A61M 39/1011* (2013.01); *A61M 39/24* (2013.01); *A61M 39/28* (2013.01); *A61M 39/288* (2013.01); *A61M 2039/0009* (2013.01); *A61M 2039/0027* (2013.01); *A61M 2039/229* (2013.01); *A61M 2039/244* (2013.01)

(56) References Cited

U.S. PATENT DOCUMENTS

| | | | |
|---|---|---|---|
| 4,447,230 A | 5/1984 | Gula et al. | |
| 4,821,996 A | 4/1989 | Bellotti et al. | |
| 7,094,216 B2 | 8/2006 | Trombley et al. | |
| 7,556,619 B2 | 7/2009 | Spohn et al. | |
| 8,147,464 B2 | 4/2012 | Spohn et al. | |
| 8,337,456 B2 | 12/2012 | Schriver et al. | |
| 8,540,698 B2 | 9/2013 | Spohn et al. | |
| 9,259,527 B2 | 2/2016 | Spohn et al. | |
| 2002/0087126 A1* | 7/2002 | Quah | A61M 39/284 604/250 |
| 2004/0064041 A1 | 4/2004 | Lazzaro et al. | |
| 2005/0113754 A1 | 5/2005 | Cowan et al. | |
| 2009/0275829 A1* | 11/2009 | Agarwal | A61M 5/007 600/433 |
| 2010/0113924 A1 | 5/2010 | Hajicek et al. | |
| 2011/0092828 A1* | 4/2011 | Spohn | A61M 5/007 600/485 |
| 2012/0123257 A1 | 5/2012 | Stokes, Jr. et al. | |
| 2013/0102975 A1 | 4/2013 | Lamb | |
| 2014/0060655 A1* | 3/2014 | Ramos | F16K 7/063 137/1 |

FOREIGN PATENT DOCUMENTS

| | | |
|---|---|---|
| WO | 2011066865 A1 | 6/2011 |
| WO | 2012155035 A1 | 11/2012 |
| WO | 2013010572 A1 | 1/2013 |
| WO | 2014047626 A2 | 3/2014 |

OTHER PUBLICATIONS

"International Search Report and the Written Opinion from PCT/US2015/034565", dated Sep. 15, 2015.
"Extended European Search Report in EP Application No. 15806874", dated Dec. 7, 2017.

\* cited by examiner

TUBING ASSEMBY

CROSS-REFERENCE TO RELATED APPLICATIONS

The present application is a U.S. national stage filing under 35 U.S.C. § 371 of International Application No. PCT/US2015/034656, filed Jun. 8, 2015, which claims priority to U.S. Provisional Patent Application No. 62/009,731, filed on Jun. 9, 2014 and entitled "Tubing Assembly", the disclosure of which is incorporated herein in its entirety.

BACKGROUND OF THE DISCLOSURE

Field of the Disclosure

The present disclosure is directed to medical fluid delivery applications and, particularly, to a tubing assembly for use with a fluid delivery system.

Description of Related Art

In many medical diagnostic and therapeutic procedures, a medical practitioner, such as a physician, injects a patient with a medical fluid. In recent years, a number of injector-actuated syringes and powered injectors for pressurized injection of fluids, such as contrast solution (often referred to simply as "contrast"), have been developed for use in procedures such as angiography, computed tomography (CT), ultrasound, and magnetic resonance imaging (MRI). In general, these powered injectors are designed to deliver a preset amount of contrast at a preset flow rate.

Automatic fluid injection mechanisms typically include at least one syringe connected to one or more powered injectors having, for example, a powered linear actuator. Typically, an operator enters settings into an electronic control system of the powered injector for a fixed volume of contrast and/or saline, and a fixed rate of injection for each. Automatic fluid injection mechanisms provide improved control over manual apparatus. Successful use of such manual devices is dependent on the skill of the medical practitioner operating the device. As in a manual system, the fluid path from the automatic fluid injection mechanism to the patient includes, for example, a source of contrast, a source of flushing fluid, typically saline, and optionally, a pressure transducer. The source of contrast may be connected to the fluid path via a valve, for example, a three-way stopcock. The source of saline and the pressure transducer may also be connected to the fluid path via additional valves, such as stopcocks.

The injected contrast and/or saline are delivered to a patient's vasculature through the catheter, needle, or IV port, inserted into the patient's body, such as the patient's arm or groin area. A dose of contrast is referred to as a bolus. Once the bolus of contrast is delivered to the desired site, that area is imaged using a conventional imaging technique, such as angiography, CT, MRI or other imaging or scanning device. The contrast becomes clearly visible against the background of the surrounding tissue.

The presence of a plurality of valves, stopcocks, and various other tubing members often complicates the setup for filling the fluid delivery system with fluid and/or for delivering the fluid from the fluid delivery system to the patient. For example, certain fluid passages must be blocked or disconnected during a filling procedure and/or unblocked during the delivery procedure.

SUMMARY OF DISCLOSURE

In view of the disadvantages of the existing tubing assemblies, there is a need in the art for an improved tubing assembly that overcomes the deficiencies of the prior art.

In accordance with one aspect, a tubing assembly for use with a fluid delivery system may have a first fluid line having a distal end and a proximal end for connecting to a first fluid source, a second fluid line having a distal end and a proximal end for connecting to a second fluid source, and a third fluid line having a distal end and a proximal end. A connector assembly may connect the distal end of the first fluid line and the distal end of the second fluid line to the proximal end of the third fluid line. The tubing assembly may have a tubing holder for receiving at least a portion of the third fluid line. The tubing holder may have a first portion and a second portion movable relative to the first portion to selectively block fluid flow through at least the third fluid line.

In accordance with another aspect, the first portion of the tubing holder may be connected to the second portion of the tubing holder by a hinge such that the second portion may be movable relative to the first portion between a first, open position and a second, closed position. A locking mechanism may lock the first portion and the second portion in the second, closed position. In the second, closed position, at least a portion of at least the third fluid line may be pinched or folded to block fluid flow through the third fluid line. The hinge may be a living hinge. At least one of the first portion and the second portion of the tubing holder may have a recessed cavity for receiving at least a portion of the third fluid line. The distal end of the third fluid line may have a connector port for connecting to a patient fluid path set.

In accordance with another aspect, at least one of the distal end of the first fluid line and the distal end of the second fluid line may be releasably coupled with the connector assembly. At least one of the distal end of the first fluid line and the distal end of the second fluid line may be non-releasably coupled with the connector assembly. The proximal end of the first fluid line may have a first connector with a first filling port and the proximal end of the second fluid line may have a second connector with a second filling port. At least one of the first filling port and the second filling port may have a one-way valve. A first filling port and a second filling port may be in fluid communication with the first fluid line and the second fluid line, respectively. A fourth fluid line may be in fluid communication with the first filling port, and a fifth fluid line may be in fluid communication with the second filling port. The second portion of the tubing holder may have a first section connected to the first portion of the tubing holder by a first hinge portion and a second section connected to the first portion by a second hinge portion. The first section and the second section may be independently movable between a first, open position and a second, closed position. In the second, closed position of the first section of the tubing holder, at least a portion of the third fluid line may be pinched or folded to block fluid flow through the third fluid line. In the second, closed position of the second section of the tubing holder, at least a portion of at least one of the fourth fluid line and the fifth fluid line may be pinched or folded to block fluid flow through at least one of the fourth fluid line and the fifth fluid line.

In accordance with another aspect, a tubing assembly for use with a fluid delivery system may include a first fluid line having a distal end and a proximal end, a first connector with a first filling port connected to the proximal end of the first fluid line, a second fluid line having a distal end and a proximal end, a second connector with a second filling port connected to the proximal end of the second fluid line, a third fluid line having a distal end and a proximal end, and a connector assembly for connecting the distal end of the first fluid line and the distal end of the second fluid line to the proximal end of the third fluid line. The tubing assembly may further include a tubing holder for receiving at least a portion of the third fluid line. The tubing holder may have a first portion and a second portion connected to the first portion by a hinge such that the second portion is movable relative to the first portion between a first, open position and a second, closed position. In the first, open position, the third fluid line may be unobstructed to allow fluid flow through the third fluid line and the first filling port and the second filling port are closed, for example by a one-way valve, to prevent fluid flow through the first filling port and the second filling port. In the second, closed position, at least a portion of the third fluid line may be obstructed to block fluid flow through the third fluid line. The distal end of the third fluid line may have a connector port for connecting to a patient fluid path set. A locking mechanism may be provided to lock the first portion and the second portion in the second, closed position.

In accordance with another aspect, a fluid delivery system may include a powered fluid injector, at least a first syringe and a second syringe releasably connected to the powered fluid injector, and a tubing assembly connectable to the first syringe and the second syringe for delivering fluid from the first syringe and the second syringe to a patient. The tubing assembly may include a first fluid line having a distal end and a proximal end for connecting to the first syringe, a second fluid line having a distal end and a proximal end for connecting to the second syringe, a third fluid line having a distal end and a proximal end, a connector assembly for connecting the distal end of the first fluid line and the distal end of the second fluid line to the proximal end of the third fluid line, and a tubing holder for receiving at least a portion of the third fluid line. The tubing holder may have a first portion and a second portion movable relative to the first portion to selectively block fluid flow through the third fluid line.

These and other features and characteristics of the tubing assembly, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only. As used in the specification and the claims, the singular form of "a", "an", and "the" include plural referents unless the context clearly dictates otherwise.

DETAILED DESCRIPTION

Figure 1:
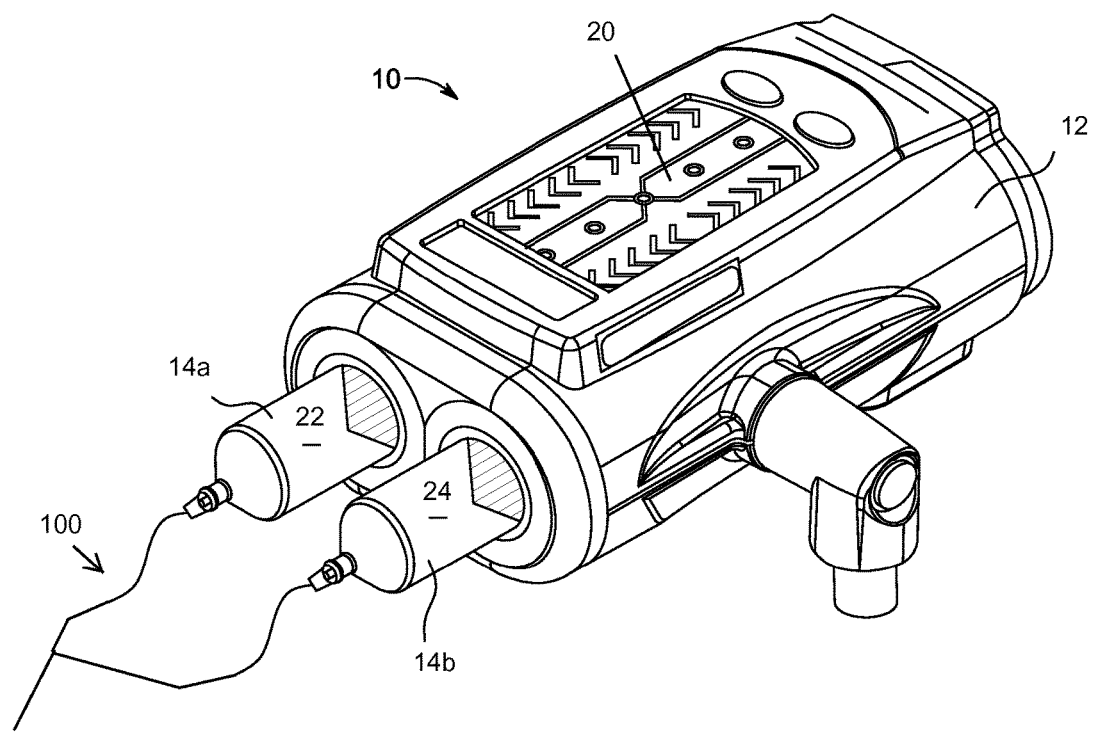
FIG. 1 is a perspective view of a fluid delivery system according to one aspect.

For purposes of the description hereinafter, the terms "upper", "lower", "right", "left", "vertical", "horizontal", "top", "bottom", "lateral", "longitudinal", and derivatives thereof shall relate to the disclosure as it is oriented in the drawing figures. When used in relation to a tubing assembly, the term "proximal" refers to a portion of a tubing assembly that is closest to a fluid delivery system when a tubing assembly is oriented for connecting to a fluid delivery system. The term "distal" refers to a portion of a tubing assembly that is farthest away from a fluid delivery system when a tubing assembly is oriented for connecting to a fluid delivery system. It is to be understood, however, that the disclosure may assume alternative variations and step sequences, except where expressly specified to the contrary. It is also to be understood that the specific devices and processes illustrated in the attached drawings, and described in the following specification, are simply exemplary aspects of the disclosure. Hence, specific dimensions and other physical characteristics related to the aspects disclosed herein are not to be considered as limiting.

Referring to the drawings in which like reference characters refer to like parts throughout the several views thereof, the present disclosure is generally directed to a tubing assembly for use with a fluid delivery system.

FIG. 1 is a perspective view of a fluid delivery system 10 for use with a tubing assembly 100 (hereinafter referred to as "the tubing assembly 100") according to one aspect. The fluid delivery system 10 is adapted for delivering one or more fluids to a patient during a medical injection procedure. For example, the fluid delivery system 10 may be used during an angiographic, CT, MRI, or a similar medical imaging procedure to inject a contrast solution and/or a common flushing agent, such as saline, into the body of a patient. An example of such a fluid injection or delivery system is disclosed in U.S. patent application Ser. No. 09/982,518, filed on Oct. 18, 2001, now issued as U.S. Pat. No. 7,094,216 on Aug. 22, 2006, and assigned to the assignee of the present application, the disclosure of which is incorporated herein by reference in its entirety. Additional examples of fluid delivery systems are disclosed in the following references: U.S. patent application Ser. No. 10/825,866, filed on Apr. 16, 2004, now issued U.S. Pat. No. 7,556,619 on Jul. 7, 2009; U.S. patent application Ser. No. 12/437,011, filed May 7, 2009, now issued U.S. Pat. No. 8,337,456; U.S. patent application Ser. No. 12/476,513, filed Jun. 2, 2009, now issued U.S. Pat. No. 8,147,464; and U.S. patent application Ser. No. 11/004,670, filed on Dec. 3, 2004 now issued as U.S. Pat. No. 8,540,698, each of which are assigned to the assignee of the present application and the disclosures of which are incorporated herein by reference in their entireties. The tubing assembly 100 is generally adapted to interface with one or more components of the fluid delivery system 10 to aid in filling the fluid delivery system with one or more fluids or with the delivery of one or more fluids from the fluid delivery system to the patient.

The fluid delivery system 10 generally includes a powered fluid injector 12 that is adapted to support and actuate a syringe 14a storing a first injection fluid 22 for injection to a patient during a medical imaging procedure. The fluid delivery system 10 further includes a second injection fluid 24 stored in a second syringe 14b that may be mixed with the first injection fluid 22 or delivered separately to the patient. In some aspects, the second injection fluid 24 may be delivered by way of a pump, such as a syringe, a piston pump, or a peristaltic pump. The injector 12 and the pump may be used to supply the first injection fluid 22 and/or the second injection fluid 24 under pressure to the tubing assembly 100 and, ultimately, the patient. In one aspect, the second injection fluid 24 may be delivered by way of a second powered injector, as described in greater detail herein. The injector 12 and/or the pump may be controlled by an injection protocol in a fluid control module 20 and/or a hand controller to supply the first and second injection fluids 22, 24 at discrete and preselected flow rates.

The injector 12 is operatively associated with a fluid control module 20. The fluid control module 20 may be adapted for controlling the operation of the fluid delivery system 10 by allowing the user to manually select the injection parameters, or select a pre-defined injection protocol. Alternatively, this functionality may reside with an external control unit or with the powered injector 12. In various embodiments, the fluid control module 20 controls, for example, filing of the syringes 14a, 14b, the injection pressure, the volume of the first and/or second injection fluids 22, 24 to be delivered to the patient, and/or the ratio of the first injection fluid 22 relative to the second injection fluid 24. In various embodiments, pre-filled syringes may be used during an injection protocol, thereby eliminating the requirement of the fluid control module 20 filling the syringes 14a, 14b.

The fluid delivery system 10 is generally adapted to connect to the tubing assembly 100 for delivering the first and/or second injection fluids 22, 24 to the patient or filling the fluid delivery system 10 with the first and/or second injection fluids 22, 24. In one aspect, the tubing assembly 100 may be connected to the powered injector 12 by way of one or more fluid path elements, such as tubing, valves, or other structures adapted for flowing fluid between the tubing assembly 100 and the powered injector 12 and/or the pump 13. In other embodiments, the tubing assembly 100 may be attached directly to the exit ports of syringes 14a, 14b. The flow of the first and second injection fluids 22, 24 may be regulated by the fluid control module 20 which regulates the delivery of the first and second injection fluids 22, 24 to the patient based on user selected injection parameters, such as total injection volume and ratio of the first and second injection fluids 22, 24. In specific embodiments, the flow of the first and second injection fluids 22, 24 may be controlled, in part, by a tubing assembly as described herein.

Figure 2:
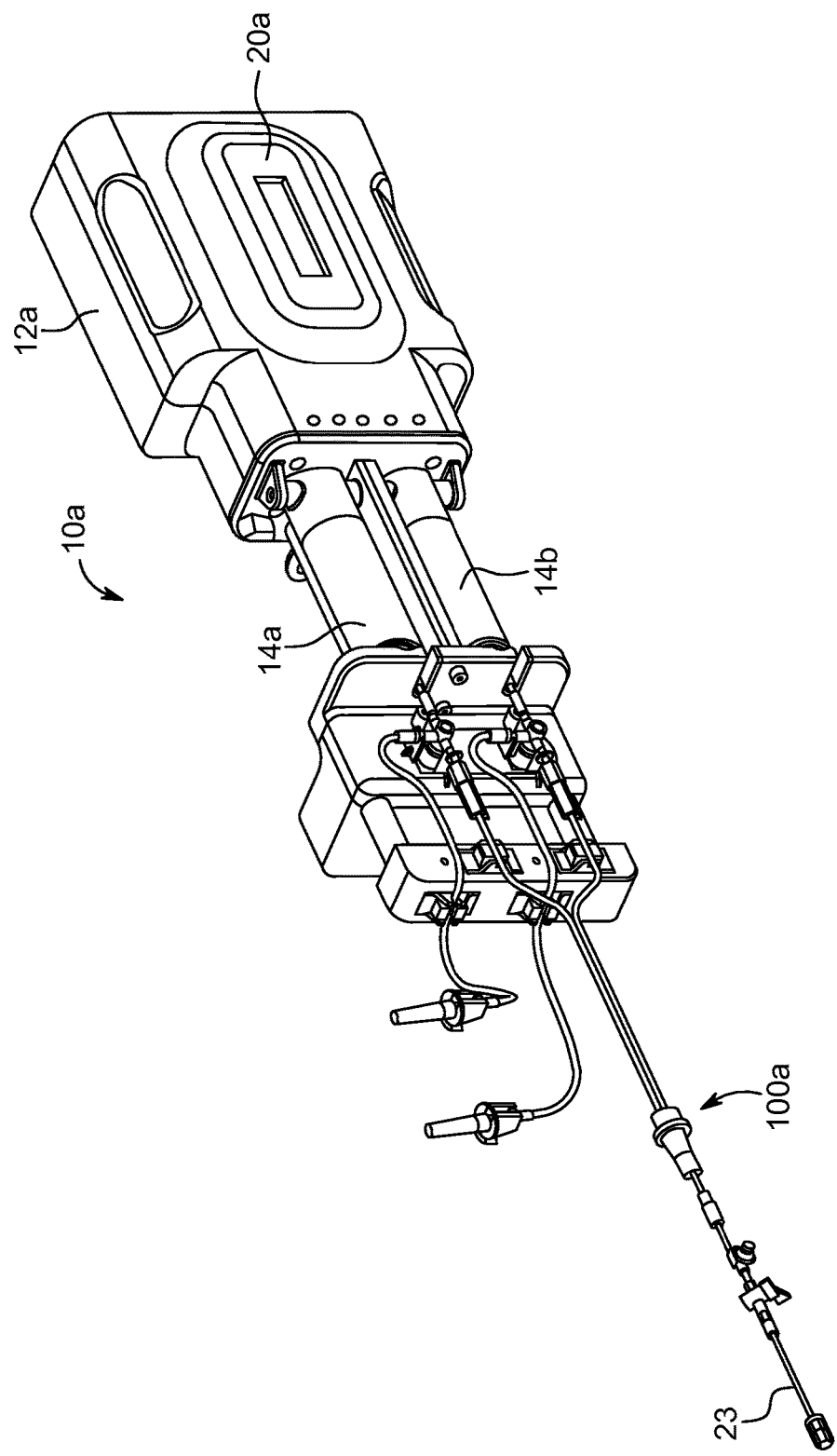
FIG. 2 is a perspective view of a fluid delivery system according to another aspect.

FIG. 2 illustrates an alternative aspect of a fluid delivery system 10a having a powered fluid injector 12a adapted to interface with two syringes 14a, 14b filled with the first injection fluid 22 and the second injection fluid 24 (shown in FIG. 1), respectively, or which may be fluidly connected to a source of the first injection fluid 22 and a source of the second injection fluid 24. The injector 12a is desirably at least a dual-syringe injector, wherein two fluid delivery syringes are oriented in a side-by-side or other relationship and which are separately actuated by respective piston elements associated with the injector 12a. In another aspect, the injector 12a may be a dual-pump injector, wherein two pumps, such as piston pumps and/or peristaltic pumps, are separately actuated and controlled. The injector 12a may be operatively associated with a fluid control module 20a.

With continued reference to FIG. 2, the tubing assembly 100a may be interfaced with the injector 12a in a similar manner to that described previously in connection with the fluid delivery system 10 described with reference to FIG. 1. The tubing assembly 100a is generally adapted to fluidly connect to a first syringe 14a having the first injection fluid 22, such as a contrast solution. The tubing assembly 100a is further generally adapted to fluidly connect to a second syringe 14b having the second injection fluid 24, such as saline. The first and second syringes 14a, 14b may have the same or a different size relative to each other. In certain aspects, one of the first syringe 14a and the second syringe 14b may be larger relative to the other of the first syringe 14a and the second syringe 14b to receive a larger volume of fluid therein. The flow of the first injection fluid 22 from the first syringe 14a and the second injection fluid 24 from the second syringe 14b may be regulated by the fluid control module 20a, which controls the various valves, pistons, and flow regulating structures to regulate the delivery of first and second injection fluids 22, 24 to the patient based on user selected injection parameters, such as total injection volume and ratio of contrast solution and saline. The tubing assembly 100a further connects to a single-patient disposable fluid path set 23 which is associated with the patient for supplying the first and second injection fluids 22, 24 to the patient. A suitable multi-syringe fluid injector for use with the above-described system is described in U.S. patent application Ser. No. 13/386,765, filed on Jan. 24, 2012, which published as U.S. patent application Publication No. 2012/0123257, and is assigned to the assignee of the present application, the disclosure of which is incorporated herein by reference in its entirety. Other relevant multi-fluid delivery systems are found in U.S. patent application Ser. No. 10/159,592, filed on May 30, 2002 (published as US 2004/0064041), U.S. patent application Ser. No. 10/722,370, filed Nov. 25, 2003 (published as US 2005/0113754), and International Patent Application No. PCT/US2012/037491, filed on May 11, 2012 (published as WO 2012/155035), all of which are assigned to the assignee of the present application, and the disclosures of which are incorporated herein by reference.

In yet another aspect, a three-fluid delivery system (not shown) may be provided. Similar to power-operated fluid delivery systems described with reference to FIGS. 1-2, a three-fluid delivery system may include a first injector or pump adapted to deliver a first injection fluid 22, such as a contrast medium, a second injector or pump adapted to deliver a second injection fluid 24, such as saline, and a third injector or pump adapted to deliver a third injection fluid. A fluid path set is provided for delivering and mixing the first, second, and third injection fluids in a desired ratio prior to being delivered to a patient. An exemplary three-fluid delivery system is disclosed in FIGS. 60-62 of U.S. patent application Publication No. 2012/0123257 discussed above.

In another aspect, a manually-controlled fluid delivery system (not shown) may be provided. Similar to power-operated fluid delivery systems described with reference to FIGS. 1-2, a manually-controlled fluid delivery system may include a first injector adapted to actuate a first syringe storing a first injection fluid 22, such as a contrast medium, for injection to a patient during a medical procedure. The manually-controlled fluid delivery system may also include a second injector adapted to actuate a second syringe storing a second injection fluid 24, such as saline. A fluid path set is provided for delivering and mixing the first injection fluid 22 and the second injection fluid 24 in a desired ratio prior to being delivered to a patient. An exemplary manually-controlled fluid delivery system is disclosed in U.S. patent application Ser. No. 13/755,883, filed Jan. 31, 2013, assigned to the assignee of the present application, the disclosure of which is incorporated herein by reference.

The following operational discussion of the tubing assembly 100 will be with exemplary reference to a fluid injection procedure involving the fluid delivery system 10 and how the tubing assembly 100 improves the filling and delivery process of the fluid delivery system 10. In typical fluid injection procedures, the first injection fluid 22 is contrast solution and the second injection fluid 24 or flushing agent is saline. One of ordinary skill in the art will appreciate that, depending on the specific medical procedure, various other medical fluids can be used as the first injection fluid 22 and the second injection fluid 24.

Figure 3:
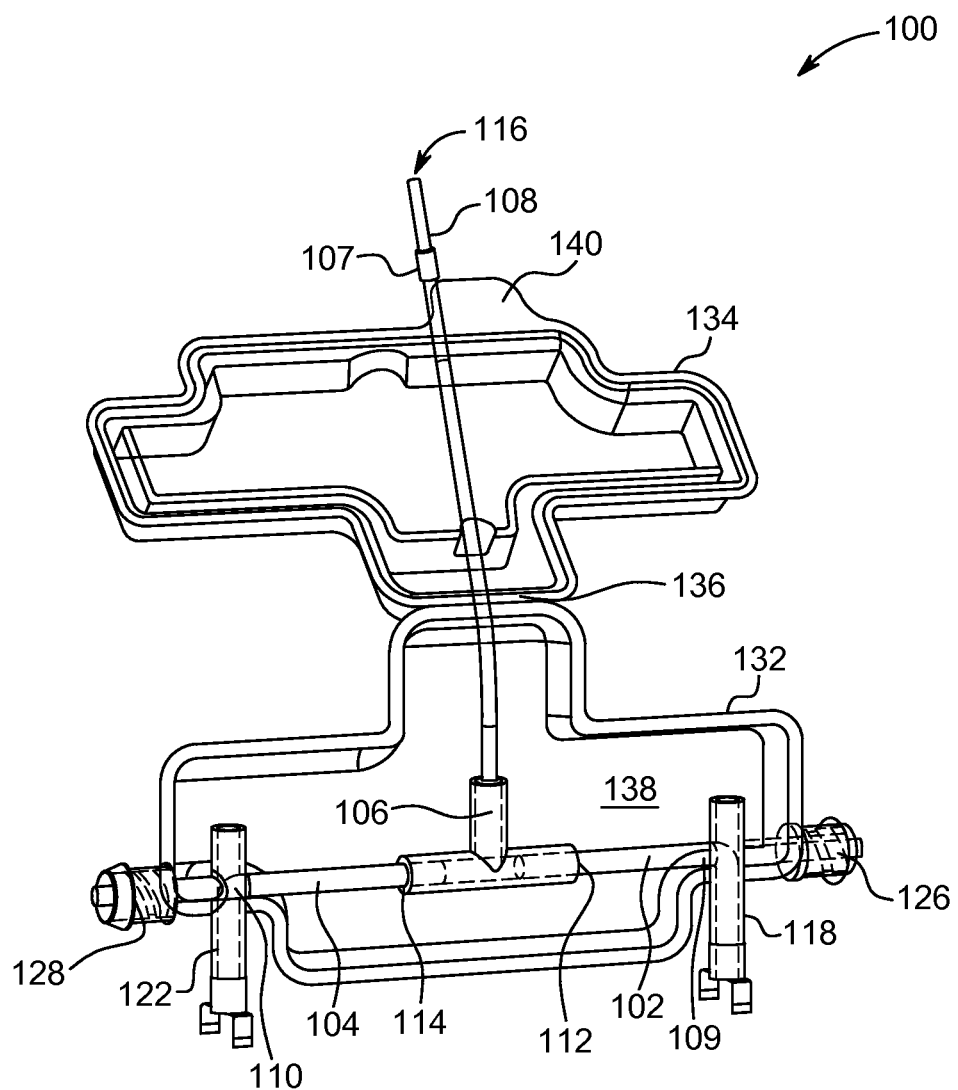
FIG. 3 is a perspective view of a tubing assembly for use with a fluid delivery system in accordance with one aspect.

With reference to the embodiment described in FIG. 3, the tubing assembly 100 includes a first fluid line 102 in fluid communication at its proximal end 109 with the source of the first injection fluid 22 (shown in FIG. 1) and a second fluid line 104 in fluid communication at its proximal end 110 with the source of the second injection fluid 24 (shown in FIG. 1). First and second fluid lines 102, 104 act as fluid conduits for delivering the first and second injection fluid 22, 24, respectively, from the source of each respective fluid. The proximal ends of the first fluid line and the second fluid line 104 may each include a connector, such as a luer connector, to fluidly connect the proximal end of the first fluid line 102 and the second fluid line 104 to a first and a second syringe 14a, 14b, respectively. Distal ends 112, 114 of each of the first and second fluid lines 102, 104 are in fluid communication with a fluid connector assembly 106 that combines the first and second fluid lines 102, 104 into a single fluid outlet line 108. In some aspects, a distal end 116 of the fluid outlet line 108 has a connector 117 for coupling the fluid outlet line 108 with the single-patient disposable fluid path set 23 (shown in FIG. 2).

With continued reference to FIG. 3, the first and second fluid lines 102, 104 may be releasably or non-releasably coupled with the fluid connector assembly 106. For example, at least one of the first and second fluid lines 102, 104 may have a connector (not shown), such as a luer-type connector, that is releasably connected to a corresponding connector provided on the fluid connector assembly 106. Alternatively, at least one of the first and second fluid lines 102, 104 may be non-releasably bonded with the fluid connector assembly 106, such as by a thermal bonding, adhesive bonding, or a molding technique. The tubing assembly 100 is configured to allow the passage of fluid therethrough, for example from the proximal end of the first and second fluid lines 102, 104 through the fluid connector assembly 106 toward the distal end of the 116 of the fluid outlet line 108. One or more valves may be provided within the tubing assembly 100 to selectively block the passage of the first and/or second injection fluid 22, 24 through the tubing assembly 100. For example, a one-way valve 107 may be provided on the fluid outlet line 108 to prevent the contrast and/or saline from flowing back into the fluid connector assembly 106. Alternatively, one or more one-way valves may be provided in one or more of the first and second fluid lines 102, 104.

Figure 4:
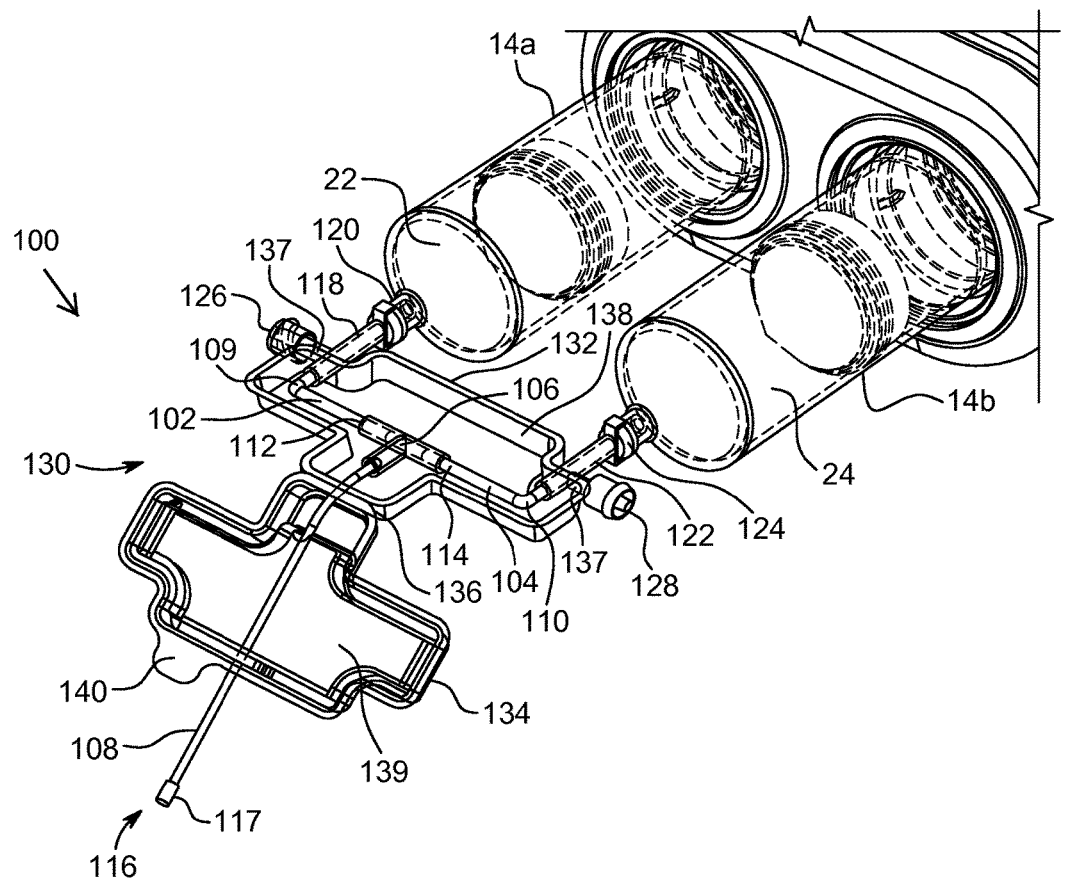
FIG. 4 is a perspective view of the tubing assembly of FIG. 3 shown in connection with a fluid delivery system with a tubing holder in a first position.

With reference to FIG. 4 showing a further aspect of the tubing assembly 100 attached to an embodiment of a power fluid injector of a fluid delivery system, the proximal end 109 of the first fluid line 102 has a first connector 118 configured for connecting to an outlet 120 of the first syringe 14a. Similarly, the proximal end 110 of the second fluid line 104 has a second connector 122 configured for connecting to an outlet 124 of the second syringe 14b. In some aspects, the connection between the first and second connectors 118, 122 with the respective outlets 120, 124 of the first and second syringes 14a, 14b is releasable such that the tubing assembly 100 can be removed from the syringes 14a, 14b. In some aspects, the first and second connectors 118, 122 are connected with the respective first and second syringes 14a, 14b by way of a threaded connection, such as a luer-type connection. In other aspects, the first and second connectors 118, 122 are connected with the respective first and second syringes 14a, 14b by a clip connection, or any other mechanical connection recognized in the medical arts.

The first connector 118 has a filling port 126 configured for connecting to a source of first fluid 22 (not shown in FIG. 4) to facilitate filling of the first syringe 14a. The filling port 126 may have a valve structure, such as a one-way valve or a stopcock, to prevent a delivery of fluid through the filling port 126 during an injection procedure. Similarly, the second connector 122 has a filling port 128 configured for connecting to a source of second fluid 24 (not shown in FIG. 4) to facilitate filling of the second syringe 14b. The filling port 128 may have a valve structure, such as a one-way valve or a stopcock, to prevent a delivery of fluid through the filling port 128 during an injection procedure. In some aspects, instead of the valve structure, the fluid lines extending from the first and second fluid lines 102, 104 to the filling port 128 may be pinched or folded at a pinch point 137 or other portion of a tubing holder 130 to prevent a delivery of fluid through the filling ports 126, 128 during an injection procedure.

With continued reference to FIG. 4, the tubing assembly 100 has the tubing holder 130. The tubing holder 130 has a first portion 132 and a second portion 134 connected together by a hinge 136. In some aspects, the hinge 136 may be a living hinge that allows the first and second portions 132, 134 of the tubing holder 130 to move between an open position (shown in FIG. 4) and a closed position (shown in FIG. 5). At least one of the first portion 132 and the second portion 134 may have a cavity that is shaped and configured for receiving at least a portion of the tubing of the tubing assembly 100. In some aspects, the first portion 132 of the tubing holder 130 has a first recessed cavity 138 for retaining at least a portion of the tubing, including, for example, at least one of the first fluid line 102, the second fluid line 104, the fluid connector assembly 106, the first and second connectors 118, 122, and the fluid outlet line 108. Similarly, the second portion 134 may have a second recessed cavity 139 for retaining at least a portion of the tubing, including, for example, at least one of the first fluid line 102, the second fluid line 104, the fluid connector assembly 106, the first and second connectors 118, 122, and the fluid outlet line 108. For example, in one aspect, at least a portion of the first and second connectors 118, 122 may be retained within or connected to the first portion 132 of the tubing holder 130. The first and second connectors 118, 122 may be retained within the first portion 132 at a distance that corresponds to the distance between the outlets 120, 124 of the first and second syringes 14a, 14b. In this manner, connection of the tubing assembly 100 with the fluid injection system 10 is facilitated. Alternatively, the first and second connectors 118, 122 may be retained at a distance other than the distance between outlets 120, 124 and the tubing assembly 100 may further have a pair of respective flexible tubing sections linking connectors 118 and 122 to outlets 120 and 124, respectively. In some aspects, the tubing holder 130 may be made from a plastic material, such as by molding. In other aspects, the tubing holder 130 may be made from a transparent or translucent material to allow the tubing to be visualized.

With continued reference to FIG. 4, in an open position, the first and second portions 132, 134 of the tubing holder 130 are arranged such that fluid flow through the fluid outlet line 108 is unobstructed. In this configuration, fluid can be delivered from the fluid delivery system 10 to the patient through the tubing assembly 100. The second portion 134 of the tubing holder 130 is movable to a second, closed position, by folding the second portion 134 over the first portion 132 along the hinge 136. In this manner, the first and second portions 132, 134 of the tubing holder 130 may be arranged in a clamshell configuration. The first and second portions 132, 134 may be releasably locked together in the second, closed position shown in FIG. 5. For example, in some aspects, a releasable locking mechanism 141 may be provided to retain the second portion 134 in a locked configuration relative to the first portion 132. In certain aspects, the locking mechanism 141 may be a groove in one of the first and second portions 132, 134 that receives a projection in the other of the first and second portions 132, 134.

Figure 5:
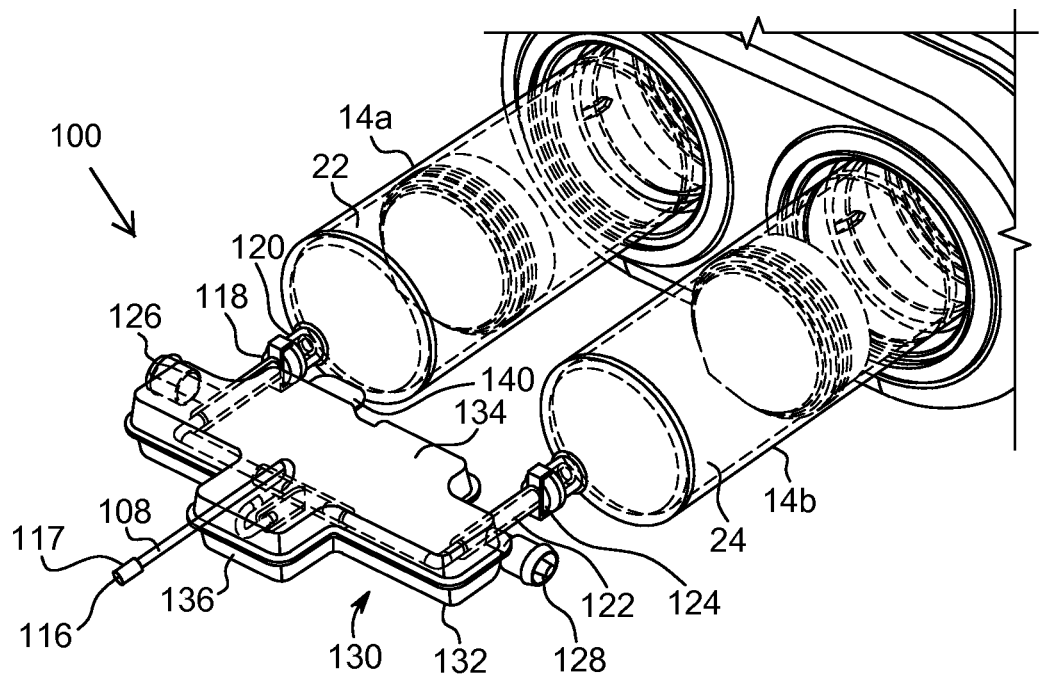
FIG. 5 is a perspective view of the tubing assembly of FIG. 4 shown in connection with the fluid delivery system with the tubing holder in a second position.

With reference to FIG. 5, in the closed position, the first and second portions 132, 134 of the tubing holder 130 prevent the fluid flow through the fluid outlet line 108. In some aspects, the folding of the tubing holder 130 causes the fluid outlet line 108 to be folded, pinched, or become otherwise obstructed to prevent fluid from flowing therethrough. Furthermore, in certain embodiments, at least one the first fluid line 102 and the second fluid line 104 may be obstructed in the closed position, for example, to prevent the first injection fluid from flowing from the first syringe 14a into the second syringe 14b and/or to prevent the second injection fluid 24 from flowing from the second syringe 14b into the first syringe 14a during filling. The point of obstruction in the at least one the first fluid line 102 and the second fluid line 104 may be in the fluid line portion(s) located between the filling ports 126, 128. In this manner, the syringes 14a, 14b may be filled with the first and second injection fluids 22, 24 from an external fluid source (not shown), but obstruction of fluid flow in the fluid line between filling ports 126, 128 prevents flow between the syringes 14a, 14b. For example, the fluid outlet line 108 and/or at least one of the at least one the first fluid line 102 and the second fluid line 104 may be folded or pinched at a position where the first portion 132 contacts the second portion 134 of the tubing holder when in the second position. After at least one of the syringes 14a, 14b are filled, the first and second portions 132, 134 can be unlocked by releasing and unfolding the second portion 134 from the first portion 132 along the hinge 136. In some aspects, the tubing holder 130 (i.e. first portion 132 and second portion 134) may be removably connected with the tubing of the tubing assembly 100 such that the tubing holder 130 may be removed after the tubing assembly 100 is attached to the fluid delivery system 10 and the filling procedure is completed. A tab 140a, 140b may be provided on at least one of the first portion 132 and the second portion 134a, 134b of the tubing holder 130 to facilitate the separation or unlocking of the first portion 132 from the second portion 134a, 134b.

In certain embodiments, tubing assembly 100 may be produced in the closed position with the fluid outlet line 108 obstructed by the closure of the first portion 132 and the second portion 134 and the fluid outlet line 108 coiled, folded or otherwise enclosed within the cavity formed by first and second recessed cavities 138 and 139. According to this embodiment, a user would unpack the tubing assembly 100, for example in a sterilized state from sterility maintaining packaging material, and attach tubing assembly 100 to the syringes 14a, 14b associated with a fluid injector, for example by connectors 118, 124. The user would then connect one or more fluid containers to fluid ports 126, 128 and operate the fluid injector to fill syringes 14a, 14b, for example with contrast and saline, respectively. After the syringes are filled, the user may then move the tubing assembly 100 from the closed position to the open position by unlocking and separating the first portion 132 from the second portion 134 around hinge 136. By opening the tubing assembly, fluid communication between the interior of syringes 14a, 14b and the distal end of fluid outlet line 108 is established. The fluid outlet line 108 may be removed from the cavity to ensure unobstructed fluid communication, for example be extending the folded or pinched portion of fluid outlet line 108. The user may then prime the system, if necessary, and then at the fluid outlet line 108 to the patient line for the fluid injection procedure.

Figure 6:
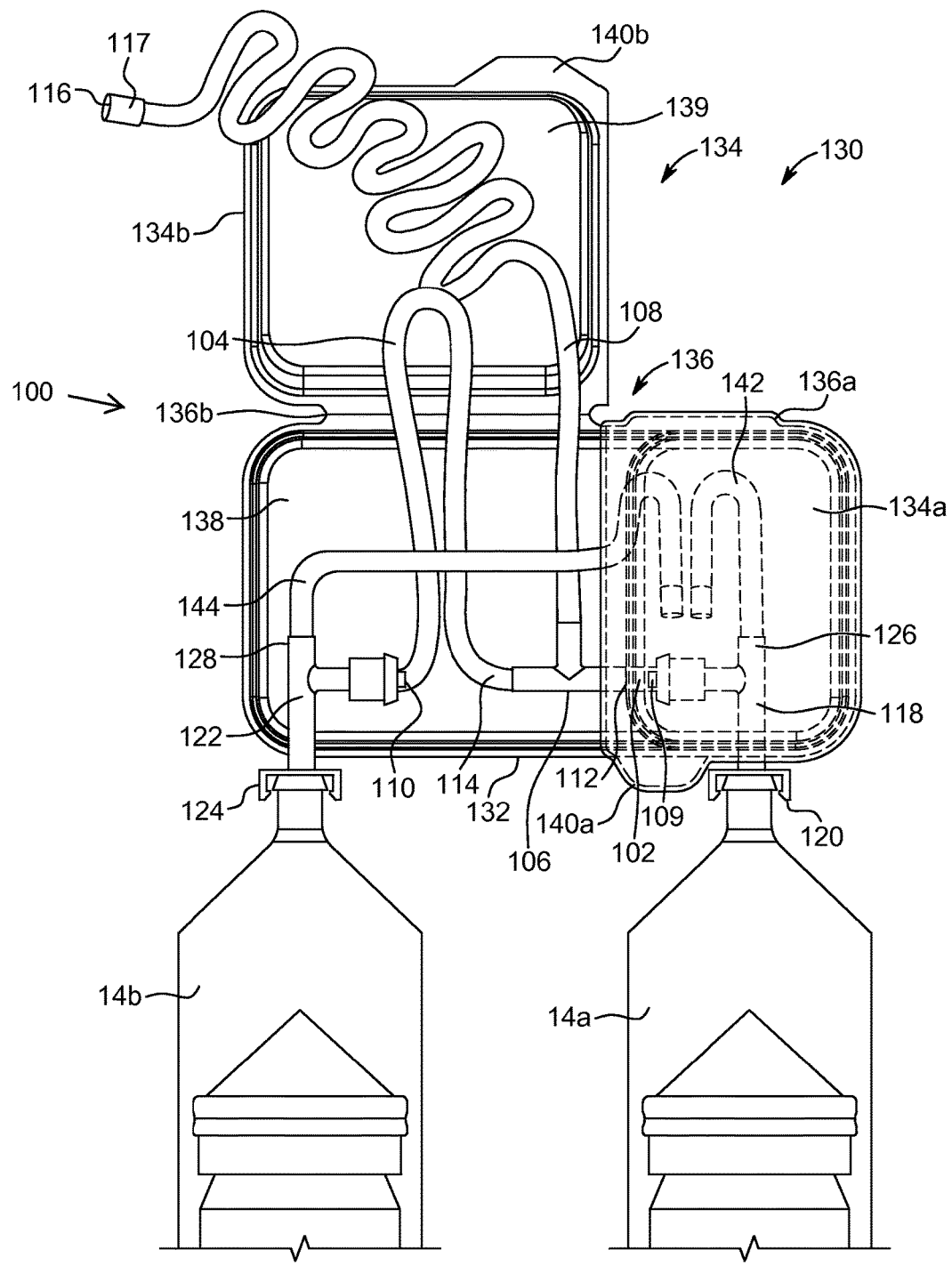
FIG. 6 is a schematic view of a tubing holder according to a further aspect.

With reference to FIG. 6, the tubing assembly 100 has a tubing holder 130 shown in accordance with another aspect. In this embodiment, tubing holder 130 has a first portion 132 and a second portion 134 connected together by a hinge 136. The second portion 134 is split into a first section 134a and a second section 134b, each of which is connected with the first portion 132 by way of a first hinge portion 136a and a second hinge portion 136b, respectively. In some aspects, the first and second hinge portions 136a, 136b may be living hinges that allow the first and second sections 134a, 134b of the second portion 134 to move between an open position and a closed position relative to the first portion 132. At least one of the first portion 132 and the second portion 134, including at least one of first and second sections 134a, 134b sections 134a, 134b of the second portion 134, may have a cavity that is shaped and configured for receiving at to enclose least a portion of the tubing when in the closed position. In some aspects, the first portion 132 of the tubing holder 130 has a first recessed cavity 138 for retaining at least a portion of the tubing, including, for example, at least one of the first fluid line 102, the second fluid line 104, the fluid connector assembly 106, the first and second connectors 118, 122, and the fluid outlet line 108. Similarly, the second portion 134 may have a second recessed cavity 139 for retaining at least a portion of the tubing, including, for example, at least one of the first fluid line 102, the second fluid lines 104, the fluid connector assembly 106, the first and second connectors 118, 122, and the fluid outlet line 108. For example, in one aspect, at least a portion of the first and second connectors 118, 122 is connected to the first portion 132 of the tubing holder 130. The first and second connectors 118, 122 may be retained within the first portion 132 at a distance that corresponds to the distance between the outlets 120, 124 of the first and second syringes 14a, 14b. In this manner, connection of the tubing assembly 100 with the fluid injection system 10 is facilitated.

With continued reference to FIG. 6, in a partially open position, the second section 134b of first portion 132 and second portion 134 of the tubing holder 130 are arranged in an open position such that fluid flow through the fluid outlet line 108 is unobstructed (i.e., not folded or pinched by contact between second section 134b and second portion 134. In this configuration, fluid can be delivered from the fluid delivery system 10 to the patient through the tubing assembly 100. The first and second sections 134a, 134b of the second portion 134 are independently movable to a second, closed position, by folding one or both of the first and second sections 134a, 134b of the second portion 134 over the first portion 132 along the first and second hinges 136a, 136b. In this manner, the first portion 132 and one or both of the first and second sections 134a, 134b may be arranged in a clamshell configuration. The first portion 132 and one or both of the first and second sections 134a, 134b may be locked together in the second, closed position. For example, in some aspects, a locking mechanism may be provided to retain one or both of the first and second sections 134a, 134b of the second portion 134 in a locked configuration relative to the first portion 132.

With continued reference to FIG. 6, a fourth and a fifth fluid line 142, 144 are provided at an inlet to the first and second filling ports 126, 128, respectively. In the closed position, the first portion 132 and the first section 134a of the second portion 134 prevent the fluid flow through at least one of the fourth and fifth fluid lines 142, 144. In some aspects, folding the second section 134a of the second portion 134 causes at least one of the fourth and fifth fluid lines 142, 144 to be folded, pinched, or become otherwise obstructed to prevent fluid from flowing therethrough. According to certain aspects, filling the syringes 14a, 14b may be accomplished by moving the first portion 132 and the first section 134a of the second portion 134 to the open position around first hinge 136a to access fourth and fifth fluid lines 142, 144 from in the cavity formed by the enclosure between the first portion 132 and the first section 134a of the second portion 134. The fourth and fifth fluid lines 142, 144 may then be connected, for example by a luer connection or other medical connection, to fluid containers, such as a contrast bottle and/or a saline bag (not shown) to form a fluid connection between syringes 14a, 14b and the fluid containers via fourth and a fifth fluid line 142, 144 via the first and second filling ports 126, 128. The fluid injector may then be operated to fill syringes 14a, 14b, for example by moving the pistons in the syringe in a proximal direction to draw the fluid into each syringe. Upon completion of the filling operation, the second section 134a of the second portion 134 may be moved to the closed position which causes at least one of the fourth and fifth fluid lines 142, 144 to be folded, pinched, or become otherwise obstructed to prevent fluid from flowing therethrough. In addition, the first portion 132 and the second section 134b of the second portion 134 prevent the fluid flow through the fluid outlet line 108 and/or at least one of the first and second fluid lines 102, 104 for example during a filling operation to fill the syringes 14a,14b with fluids. In some aspects, folding the second section 134b of the second portion 134 causes the fluid outlet line 108 and/or at least one of the first and second fluid lines 102, 104 to be folded, pinched, or become otherwise obstructed to prevent fluid from flowing therethrough. Furthermore, at least one of the first fluid line 102 and the second fluid line 104 is obstructed to prevent the first injection fluid from flowing from the first syringe 14a into the second syringe 14b and/or to prevent the second injection fluid 24 from flowing from the second syringe 14b into the first syringe 14a during filling. In this manner, the syringes 14a, 14b may be filled with the first and second injection fluids 22, 24 from an external fluid source (not shown). After the syringes 14a, 14b are filled, the first portion 132 and the second section 134b of the second portion 134 can be unlocked by unfolding the second section 134b of the second portion 134 from the first portion 132 along the second hinge 136b. Furthermore, the first portion 132 and the first section 134a of the second portion 134 are locked by folding the first section 134a of the second portion 134 over the first portion 132 along the first hinge 136a to prevent fluid from flowing through the fourth and fifth fluid lines 142, 144. In some aspects, at least a portion of the tubing holder 130 may be removably connected with the tubing of the tubing assembly 100 such that at least a portion of the tubing holder 130 may be removed after the tubing assembly 100 is attached to the fluid delivery system 10 and the filling procedure is completed, for example, the first portion 132 and the second section 134b of the second portion 134 removed prior to the injection procedure.

In a further aspect, the second portion 134 may have a plurality of sections. For example, the second portion 134 may be divided into a plurality of sections, such as three sections, where each of the sections is connected with the first portion 132 by way of a corresponding hinge portion that connects the section of the second portion 134 with the first portion 132. Each of the plurality of sections of the second portion 134 may be independently movable between a first, open position, where each of the plurality of sections may be independently disconnected or disengaged from the first portion 132 and a second, closed position, where the plurality of sections is connected to or engaged with the first portion 132. In one aspect, the plurality of sections of the second portion 134 may be connected to or engaged with the first portion 132 by selectively folding the plurality of sections of the second portion 134 over the first portion 132 along the respective hinges. In one aspect, a first, second, and third section of the second portion 134 may independently fold, pinch, or otherwise obstruct a fluid flow through one or more of the first fluid line 102, the second fluid line 104, the fourth fluid line 142, the fluid outlet line 108, and the fifth fluid line 144, respectively, to prevent fluid from flowing therethrough.

According to various embodiments of the tubing assembly described herein, one or more of the hinge features 134 (such as the first hinge 134a and the second hinge 134b) may be omitted and the corresponding features of the first portion 132 and the second portion 134 (and various sections of each, thereof) may be connected, for example by a releasable snap fit. At least one of the first portion 132 and the second portion 134 may be selectively, disconnectedly removed from the other of the second portion 134 and the first portion 132, for example when access is required to the one or more fluid lines within the cavity formed by the portions. The disconnected portions of the tubing assembly may then be removed, leaving the tubing portions freely accessible. The portions of the first portion 132 and the second portion 134 may be reused, for example to reseal one or more of the corresponding tube, or may be discarded.

While various aspects of the tubing assembly were provided in the foregoing description, those skilled in the art may make modifications and alterations to these aspects without departing from the scope and spirit of the disclosure. For example, it is to be understood that this disclosure contemplates that, to the extent possible, one or more features of any aspect can be combined with one or more features of any other aspect. Accordingly, the foregoing description is intended to be illustrative rather than restrictive.

What is claimed is:

1. A tubing assembly for use with a fluid delivery system, the tubing assembly comprising:
    a first fluid line having a distal end and a proximal end for connecting to a first fluid source;
    a second fluid line having a distal end and a proximal end for connecting to a second fluid source;
    a third fluid line having a distal end and a proximal end;
    a connector assembly for connecting the distal end of the first fluid line and the distal end of the second fluid line to the proximal end of the third fluid line; and
    a tubing holder for receiving at least a portion of the third fluid line, the tubing holder having a first portion and a second portion the tubing holder further comprising a first connector having a first filling port and a second connector having a second filling port, wherein the proximal end of the first fluid line is fluidly connected to the first connector and the proximal end of the second fluid line is fluidly connected to the second connector;
    wherein the first portion of the tubing holder is connected to the second portion of the tubing holder by a hinge such that the second portion is movable relative to the first portion between a first, open position and a second, closed position;

wherein, when the tubing holder is in the second, closed position, the at least the portion of the third fluid line is pinched or folded by the first portion and the second portion to block the fluid flow through the third fluid line.

2. The tubing assembly of claim 1, further comprising a locking mechanism to reversibly lock the first portion and the second portion of the tubing holder in the second, closed position.

3. The tubing assembly of claim 1, wherein the hinge is a living hinge.

4. The tubing assembly of claim 1, wherein at least one of the first portion and the second portion of the tubing holder has a recessed cavity for receiving the at least the portion of the third fluid line.

5. The tubing assembly of claim 1, wherein the distal end of the third fluid line has a connector port for connecting to a patient fluid path set.

6. The tubing assembly of claim 1, wherein at least one of the distal end of the first fluid line and the distal end of the second fluid line is releasably coupled with the connector assembly.

7. The tubing assembly of claim 1, wherein at least one of the distal end of the first fluid line and the distal end of the second fluid line is non-releasably coupled with the connector assembly.

8. The tubing assembly of claim 1, wherein at least one of the first filling port and the second filling port has a one-way valve.

9. The tubing assembly of claim 1, further comprising a fourth fluid line in fluid communication with the first filling port, and a fifth fluid line in fluid communication with the second filling port.

10. The tubing assembly of claim 9, wherein the hinge comprises a first hinge portion and a second hinge portion, wherein the second portion of the tubing holder has a first section connected to the first portion of the tubing holder by a first hinge portion and a second section connected to the first portion of the tubing holder by a second hinge portion.

11. The tubing assembly of claim 10, wherein the first section and the second section are independently movable between a first, open position and a second, closed position.

12. The tubing assembly of claim 11, wherein, in the second, closed position of the first section of the second portion of the tubing holder, the at least the portion of the third fluid line is pinched or folded by the first section of the second portion and the first portion of the tubing holder to block the fluid flow through the third fluid line.

13. The tubing assembly of claim 11, wherein, in the second, closed position of the second section of the second portion of the tubing holder, at least a portion of at least one of the fourth fluid line and the fifth fluid line is pinched or folded by the second section of the second portion and the first portion of the tubing holder to block fluid flow through the at least one of the fourth fluid line and the fifth fluid line.

14. The tubing assembly of claim 1, wherein the first connector and the second connector of the tubing holder are configured for connecting the tubing holder to an outlet of a first syringe and an outlet of a second syringe, respectively.

15. A tubing assembly for use with a fluid delivery system, the tubing assembly comprising:
a first fluid line having a distal end and a proximal end;
a first connector with a first filling port connected to the proximal end of the first fluid line;
a second fluid line having a distal end and a proximal end;
a second connector with a second filling port connected to the proximal end of the second fluid line;
a third fluid line having a distal end and a proximal end;
a connector assembly for connecting the distal end of the first fluid line and the distal end of the second fluid line to the proximal end of the third fluid line; and
a tubing holder for receiving at least a portion of the third fluid line, the tubing holder having a first portion and a second portion connected to the first portion by a hinge such that the second portion is movable relative to the first portion between a first, open position and a second, closed position, the tubing holder further comprising the first connector with the first filling port and the second connector with the second filling port wherein the proximal end of the first fluid line is fluidly connected to the first connector and the proximal end of the second fluid line is fluidly connected to the second connector;
wherein, in the first, open position, the third fluid line is unobstructed to allow fluid flow through the third fluid line and the first filling port and the second filling port are closed to prevent fluid flow through the first filling port and the second filling port, and
wherein, in the second, closed position, the at least the portion of the third fluid line is obstructed to block fluid flow through the third fluid line.

16. The tubing assembly of claim 15, wherein the distal end of the third fluid line has a connector port for connecting to a patient fluid path set.

17. The tubing assembly of claim 15, further comprising a locking mechanism to reversibly lock the first portion and the second portion of the tubing holder in the second, closed position.

* * * * *